United States Patent
Okamura

(10) Patent No.: US 11,919,987 B2
(45) Date of Patent: Mar. 5, 2024

(54) (METH)ACRYLOYL COMPOUND AND A METHOD FOR PREPARING THE SAME

(71) Applicant: Shin-Etsu Chemical Co., Ltd., Tokyo (JP)

(72) Inventor: Kaoru Okamura, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 343 days.

(21) Appl. No.: 17/270,940

(22) PCT Filed: Aug. 22, 2019

(86) PCT No.: PCT/JP2019/032817
§ 371 (c)(1),
(2) Date: Feb. 24, 2021

(87) PCT Pub. No.: WO2020/045225
PCT Pub. Date: Mar. 5, 2020

(65) Prior Publication Data
US 2021/0324123 A1 Oct. 21, 2021

(30) Foreign Application Priority Data

Aug. 30, 2018 (JP) ................. 2018-161673

(51) Int. Cl.
*C07C 69/587* (2006.01)
*C08F 220/40* (2006.01)
*C08J 3/075* (2006.01)
*C08L 33/06* (2006.01)

(52) U.S. Cl.
CPC ............ *C08F 220/40* (2013.01); *C08J 3/075* (2013.01); *C08L 33/06* (2013.01); *C08J 2333/06* (2013.01); *C08L 2203/02* (2013.01)

(58) Field of Classification Search
CPC .... C07C 69/587; C08F 220/54; C08F 220/14; C08F 220/40; C08F 222/385
See application file for complete search history.

(56) References Cited

U.S. PATENT DOCUMENTS

| 4,022,754 | A | 5/1977 | Howes et al. | |
| 2016/0297736 | A1* | 10/2016 | Wilczynski | C07C 67/03 |
| 2016/0297904 | A1* | 10/2016 | Berbee | C09D 123/04 |

FOREIGN PATENT DOCUMENTS

| CN | 109100918 | A * | 12/2018 | G03F 7/004 |
| JP | S50128740 | A | 10/1975 | |
| JP | H09151303 | A | 6/1997 | |
| JP | 2006193429 | A | 7/2006 | |
| JP | 2014052401 | A | 3/2014 | |
| JP | 2017500399 | A | 1/2017 | |
| WO | WO-2018039376 | A1 * | 3/2018 | A01N 37/02 |

OTHER PUBLICATIONS

English translation of International Search Report corresponding to International Patent Application No. PCT/JP2019/032817 (2 pages) (dated Nov. 12, 2019).

* cited by examiner

*Primary Examiner* — Karuna P Reddy
(74) *Attorney, Agent, or Firm* — Myers Bigel, P.A.

(57) ABSTRACT

The present invention provides a (meth)acryloyl compound suitable to prepare a medical material having beneficial hydrophilicity and sufficient strength; and a method for preparing the compound. A compound represented by the following formula (1):

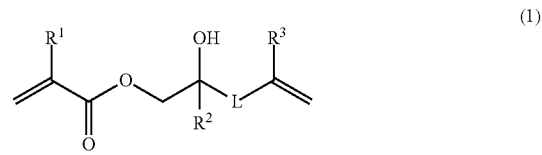

(1)

wherein $R^1$ is a hydrogen atom or a methyl group, $R^2$ is a monovalent hydrocarbon group having 1 to 6 carbon atoms, $R^3$ is a hydrogen atom or a methyl group and, L is a divalent hydrocarbon group having 2 to 10 carbon atoms and optionally having an ether bond.

18 Claims, No Drawings

(METH)ACRYLOYL COMPOUND AND A METHOD FOR PREPARING THE SAME

TECHNICAL FIELD

The present invention relates to a (meth)acryloyl compound. More specifically, the invention provides a (meth)acryloyl compound suitable for preparing a medical material and a method for preparing the compound.

BACKGROUND ART

Acryloyl compounds having hydrophilicity such as N,N-dimethylacrylamide and 2-hydroxyethyl methacrylate are known to be used for medical materials. They are compatible with other acryloyl compounds. Its (co)polymers have high transparency, strength, and hydrophilicity with water and are, accordingly, suited for use as medical materials. Patent Literatures 1 and 2 describe compounds which have a terminal unsaturated bond and a (meth)acryloyl group, as represented by the following formula (a) or (a'), for obtaining a material having a more desirable strength. Such bifunctional compounds may be used as a crosslinking component or to introduce of various functional group or functions by making use of the unsaturated bond. Further, they are suitable to be used in hydrogel material such as medical materials on account of its hydroxyl group.

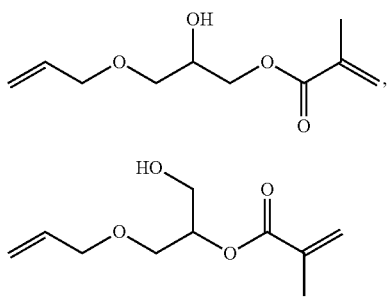

PRIOR ART LITERATURES

Patent Literatures

Patent Literature 1: Japanese Patent Application Laid-Open No. Sho 50-128740
Patent Literature 2: Japanese Patent Application Laid-Open No. 2006-193429

SUMMARY OF THE INVENTION

Problems to be Solved by the Invention

The compounds represented by the formula (a) or (a') however sometimes causes an undesirable side reaction due to high reactivity of the hydroxyl group present in its molecule, when another functional group is introduced at the unsaturated bond of the compound or a secondary crosslinked structure is formed. For example, a crosslinked structure is formed by radical addition at the unsaturated bond, a radical is added to the hydroxyl group so as to form crosslinked structure by the hydroxy radical, which may lead to an unexpected hardness (increase in a modulus of elasticity) or deteriorated hydrophilicity due to a decreased amount of the hydroxyl groups. Accordingly, these acryloyl compounds do not provide a medical material having beneficial hydrophilicity and sufficient strength.

In the aforesaid circumstances, the present invention provides a (meth)acryloyl compound suitable to prepare a medical material having beneficial hydrophilicity and sufficient strength; and a method for preparing the compound.

Means to Solve the Problems

The present inventors have carried out an intensive investigation to solve the aforesaid problems to find that a (meth)acryloyl compound having a tertiary hydroxyl group provides a (co)polymer having excellent hydrophilicity and sufficient strength, because the tertiary hydroxyl group does not react during a polymerization reaction, and have completed the present invention.

The present invention provides a (meth)acryloyl compound represented by the following formula (1):

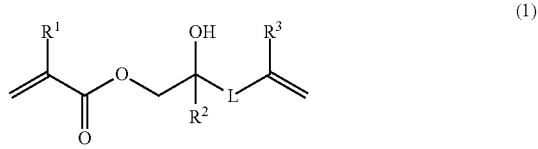

wherein $R^1$ is a hydrogen atom or a methyl group, $R^2$ is a monovalent hydrocarbon group having 1 to 6 carbon atoms, $R^3$ is a hydrogen atom or a methyl group, and L is a divalent hydrocarbon group having 2 to 10 carbon atoms and optionally having an ether bond.

The present invention further provides a method for preparing the (meth)acryloyl compound, a (co)polymer comprising a recurring unit derived from the compound, and a hydrogel and a medical material, particularly, a contact lens, each containing the (co)polymer.

Effects of the Invention

The (meth)acryloyl compound of the present invention has, in the molecule, a terminal unsaturated bond as well as a (meth)acryloyl group, so that it forms a crosslinked structure by the polymerization at the (meth)acryloyl group and at the unsaturated bond to provide a (co)polymer having a preferable strength. In addition, the compound has excellent compatibility with a hydrophilic monomer on account of the tertiary hydroxyl group of the compound. Further, the (co)polymer has excellent hydrophilicity besides the sufficient strength, because the tertiary hydroxyl group does not cause a side reaction.

DETAILED DESCRIPTION OF THE PREFERRED EMBODIMENTS

The (meth)acryloyl compound of the present invention will hereinafter be described in detail.

The compound of the present invention is a (meth)acryloyl compound represented by the aforesaid formula (1). The compound has a (meth)acryloyl group, a terminal unsaturated bond, and a tertiary hydroxyl group. The compound is excellent in compatibility with a hydrophilic monomer. A (co)polymer composed of the compound as a monomer or comprising the compound as a crosslinking agent has a preferable strength. In addition, the hydrophilic hydroxyl group is tertiary and, therefore, causes less side-reaction. On account of these characteristics, the (co)polymer has an improved strength, while having good compatibility with another hydrophilic monomer.

In the aforesaid formula (1), $R^1$ is a hydrogen atom or a methyl group, preferably a methyl group.

In the aforesaid formula (1), $R^2$ is a $C_{1-6}$ monovalent hydrocarbon group. Examples of the monovalent hydrocarbon group include alkyl groups such as a methyl group, an ethyl group, a propyl group, a butyl group, a pentyl group, and a hexyl group; cycloalkyl groups such as a cyclopentyl group and a cyclohexyl group; and aryl groups such as a phenyl group. $R^2$ is preferably a $C_{1-4}$ alkyl group, more preferably a methyl group.

In the aforesaid formula (1), $R^3$ is a hydrogen atom or a methyl group, preferably a hydrogen atom.

In the aforesaid formula (1), L is a $C_{2-10}$ divalent hydrocarbon group which may contain an ether bond. L is preferably a group represented by the following formula (2) and n stands for 1 or 2.

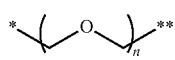

(2)

wherein the sites marked with * or ** is bonded to the carbon atom.

Examples of the $C_{2-10}$ divalent hydrocarbon group include methylene, ethylene, 1,3-propylene, 1-methylpropylene, 1,1-dimethylpropylene, 2-methylpropylene, 1,2-dimethylpropylene, 1,1,2-trimethylpropylene, 1,4-butylene, 2-methyl-1,4-butylene, 2,2-dimethyl-1,4-butylene, 3-methyl-1,4-butylene, 2,2-dimethyl-1,4-butylene, 2,3-dimethyl-1,4-butylene, 2,2,3-trimethyl-1,4-butylene, 1,5-pentylene, 1,6-hexanylene, 1,7-heptanylene, 1,8-octanylene, 1,9-nonanylene, and 1,10-decanylene groups. Examples of the group containing an ether bond include polyalkylene oxides such as polyethylene oxide, polypropylene oxide, and polyethylene-propylene oxide, preferably —CH$_2$OCH$_2$— and —CH$_2$OC$_2$H$_4$OCH$_2$—.

A method for preparing the compound represented by the aforesaid formula (1) will hereinafter be explained.

The preparation method of the present invention comprises a step of reacting an epoxy compound represented by the following formula (3),

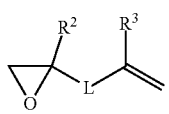

(3)

wherein $R^2$, $R^3$ and L are as defined above,
with (meth)acrylic acid to obtain the compound represented by the aforesaid formula (1). This step will hereinafter be referred to as "Step II".

The preparation method of the present invention further comprises a step of reacting an alcohol compound represented by the following formula (4):

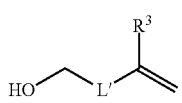

(4)

wherein $R^3$ is as defined above and L' is a single bond or a divalent hydrocarbon group which has 1 to 8 carbon atoms and may optionally have an ether bond,
with an epoxy compound represented by the following formula (5):

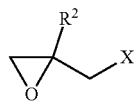

(5)

wherein $R^2$ is as defined above and X is a halogen atom, to obtain the epoxy compound represented by the aforesaid formula (3). This step will hereinafter be referred to as "Step I".

Steps I and II will hereinafter be explained in detail.
Step I.

In this step, an alcohol compound represented by the following formula (4):

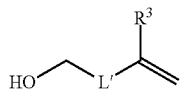

(4)

wherein $R^3$ is as defined above and L' is a single bond or a divalent hydrocarbon group which has 1 to 8 carbon atoms and may have an ether bond,
is reacted with an epoxy compound represented by the following formula (5):

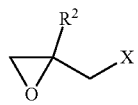

(5)

wherein $R^2$ is as defined above and X is a halogen atom, to obtain the epoxy compound represented by the aforesaid formula (3).

In the aforesaid formula (4), L' is, as defined above, a $C_{1-8}$ divalent hydrocarbon group which may optionally contain an ether bond. It is preferably the group represented by the following formula (2') wherein n' stands for 0 or 1.
When n' stands for 0, L' is a single bond in the aforesaid formula (4).

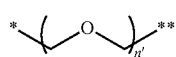

(2')

wherein the sites marked with * or ** is bonded to the carbon atom.

Thus, the group represented by the formula (4) is preferably the following (2") or (2''').

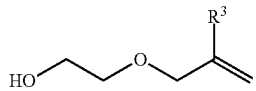

(2')

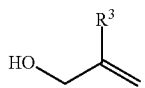

(2''')

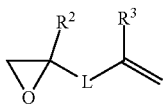

(3)

In the aforesaid formula (5), X is, as defined above, a halogen atom. Examples of the halogen atom include fluorine, chlorine, bromine, and iodine atoms.

The alcohol compound and the epoxy compound may be reacted in a conventional method. For example, 1 molar equivalent of the alcohol compound and 1 molar equivalent or more of the epoxy compound may be subjected to reaction. A reaction temperature is not particularly limited, and is preferably a temperature not exceeding a boiling temperature of a solvent to be used. For example, the reaction temperature is preferably from about 0° C. to about 120° C. The reaction may be done in the presence of a solvent or a catalyst. Any known solvent and catalyst may be used.

Examples of the catalyst include basic compounds, organophosphorus compounds, tertiary amines, and Lewis acids. Examples of the basic compounds include hydroxides of an alkali metal or alkali earth metal, such as lithium hydroxide, sodium hydroxide, potassium hydroxide, calcium hydroxide, and magnesium hydroxide. Examples of the organophosphorus compounds include tricyclohexylphosphine, tributylphosphine, trioctylphosphine, cyclohexyldiphenylphosphine, dicyclohexylphenylphosphine, butyldiphenylphosphine, dibutylphenylphosphine, octyldiphenylphosphine, dioctylphenylphosphine, and triphenylphosphine. Examples of the tertiary amines include trimethylamine, triethylamine, tripropylamine, tributylamine, diazabicycloundecene, diazabicyclononene, and 1-methylimidazole. Examples of the Lewis acids include boron trifluoride, aluminum chloride, methyldichloroaluminum, dimethylchloroaluminum, trimethylaluminum, magnesium chloride, magnesium bromide, titanium tetrachloride, dichlorotitanium bistriflate, biscyclopentadienyltitanium bistriflate, dichlorotitanium bisfluorosulfonate, tin tetrachloride, and tin (II) bistriflate. The catalyst may be used alone or in combination thereof.

Examples of the solvent include glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester solvents such as ethyl acetate, butyl acetate, amyl acetate, ethyl lactate, and methyl benzoate; aliphatic hydrocarbon solvents such as linear hexane, linear heptane, and linear octane; alicyclic hydrocarbon solvents such as cyclohexane and ethylcyclohexane; ketone solvents such as acetone, methyl ethyl ketone, and methyl isobutyl ketone; aromatic hydrocarbon solvents such as benzene, toluene, and xylene; and petroleum solvents. The solvent may be used alone or in combination thereof.

Step II

In this step, the epoxy compound represented by the following formula (3):

wherein $R^2$, $R^3$ and L are as defined above,
is reacted with (meth)acrylic acid to obtain the compound represented by the aforesaid formula (1).

The reaction may be done in a known method. For example, 1 molar equivalent of the epoxy compound and 1 molar equivalent or more of (meth)acrylic acid may be subjected to the reaction. A reaction temperature is not particularly limited, and is preferably a temperature not exceeding a boiling temperature of a solvent to be used. For example, the reaction temperature is preferably from about 0° C. to about 110° C. The reaction may be done in the presence of a solvent, a catalyst and a stabilizer. Any known solvent, catalyst and stabilizer may be used. The solvent may be those described above.

Examples of the catalyst include organometallic catalysts, basic compounds, organophosphorus compounds, amine catalysts, and Lewis acids. Examples of the basic compounds include those described above. The organometallic catalysts are not particularly limited and include (meth)acrylates such as sodium (meth)acrylate and potassium (meth)acrylate; organotin catalysts such as stannous diacetate, stannous dioctoate, stannous dioleate, stannous dilaurate, dibutyltin oxide, dibutyltin diacetate, dibutyltin dilaurate, dibutyltin dichloride, and dioctyltin dilaurate; and acetylacetone metal salts such as acetylacetone aluminum, acetylacetone iron, acetylacetone copper, acetylacetone zinc, acetylacetone beryllium, acetylacetone chromium, acetylacetone indium, acetylacetone manganese, acetylacetone molybdenum, acetylacetone titanium, acetylacetone cobalt, acetylacetone vanadium, and acetylacetone zirconium. Examples of the amine catalysts include the tertiary amines described above, and further pentamethyldiethylene triamine, triethylamine, N-methylmorpholine bis(2-dimethylaminoethyl)ether, N,N,N',N'',N''-pentamethyldiethylenetriamine, N,N,N'-trimethylaminoethyl-ethanolamine, bis(2-dimethylaminoethyl)ether, N-methyl-N',N'-dimethylaminoethylpiperazine, N,N-dimethylcyclohexylamine, diazabicycloundecene, triethylenediamine, tetramethylhexamethylenediamine, N-methylimidazole, trimethylaminoethylpiperazine, tripropylamine, tetramethylammonium salt, tetraethylammonium salt, and triphenylammonium salt. The catalyst may be used alone or in combination thereof.

Examples of the stabilizer include phenolic antioxidants, phosphorus-based antioxidants, amine-based antioxidants, and sulfur-based antioxidants. Any phenolic antioxidant may be used, and includes compounds selected from p-methoxyphenol, di-tert-butyl-p-cresol, pyrogallol, tert-butylcatechol, 4,4-thiobis(3-methyl-6-tert-butylphenol), 2,2'-methylenebis(4-methyl-6-t-butylphenol), phenolic resins and cresol resins. The phosphorus-based antioxidant is not particularly limited, and includes tris[2-[[2,4,8,10-tetrakis(1,1-dimethylethyl)dibenzo[d,f][1,3,2]dioxaphosphepin-6-yl]oxy]ethyl]amine, tris[2-[(4,6,9,11-tetra-tert-butyldibenzo[d,f][1,3,2]dioxaphosphepin-2-yl)oxy]ethyl]amine, and ethylbis(2,4-ditert-butyl-6-methylphenyl)phosphite. The amine-based antioxidant is not particularly limited, and includes tri- or tetra-$C_{1-3}$ alkylpiperidines and derivatives thereof, bis(2,2,6,6-tetramethyl-4-piperidyl)oxalate, 1,2-bis (2,2,6,6-tetramethyl-4-piperidyloxy)ethane, phenylnaphthylamine, N,N'-diphenyl-1,4-phenylenediamine, and N-phenyl-N'-cyclohexyl-1,4-phenylenediamine. The sulfur-based antioxidant is not particularly limited and includes dilaurylthiodipropionate and distearylthiodipropionate. The stabilizer may be used alone or in combination thereof.

In each of the aforesaid reactions, the end point of the reaction may be known by disappearance of a peak of a raw material compound in a conventional method, for example, by thin-layer chromatography (TLC), high-speed liquid chromatography (HPLC), or gas chromatography (GC). After completion of the reaction, purification may be performed by a conventional method. For example, an organic layer is washed with water and a solvent is removed to obtain a product. Alternatively, distillation at a reduced pressure or treatment with activated carbon may be conducted.

In an embodiment of the preparation method of the present invention, 1 molar equivalent of the alcohol compound represented by the aforesaid formula (4), 1 molar equivalent of the epoxy compound represented by the aforesaid formula (5), 1 molar equivalent of potassium hydroxide, and 100 parts by mass of n-hexane, relative to the total 100 parts by mass of the alcohol compound, the epoxy compound and the potassium hydroxide are put together and stirred at 20° C. to be allowed to react for about 4 hours, whereby the reaction is completed. The progress of the reaction may be followed by monitoring the epoxy compound or a formed compound via GC. After the completion of the reaction, the organic layer is washed with water. Then, the solvent and an unreacted raw material present in the organic layer are distilled off at a reduced pressure to obtain the epoxy compound represented by the aforesaid formula (3).

Then, 1 molar equivalent of the epoxy compound represented by the aforesaid formula (3), 2 molar equivalents of methacrylic acid, and 0.3 molar equivalent of sodium methacrylate are put together and heated at 100° C. with stirring. The reaction is completed by reacting for about 10 hours. The progress of the reaction may be followed by monitoring the epoxy compound or a formed compound via GC. After the completion of the reaction, 100 parts by mass of toluene, relative to the 100 parts by mass of the reaction substrate are added, the organic layer is washed with water. The solvent and an unreacted raw material present in the organic layer are distilled off at a reduced pressure to obtain the acryloyl compound represented by the aforesaid formula (1).

The compound of the present invention may be converted into a polymer comprising the recurring unit derived from the addition polymerization at a (meth)acrylic group. The compound of the present invention has good compatibility with another compound having a polymerizable group such as (meth)acrylic group, which will hereinafter be referred to as "a polymerizable monomer" or "a hydrophilic monomer". A copolymer with a polymerizable monomer is therefore colorless and transparent. Alternatively, the compound of the present invention may be homo-polymerized.

Since the compound of the present invention has a terminal unsaturated bond besides a (meth)acrylic group, its copolymer with a polymerizable monomer may undergo reaction at the terminal unsaturated bond to form a crosslinked structure. At this time, the tertiary hydroxyl group present in the molecule does not react, so that reduction in an equilibrium water content and an undesired increase in a modulus of elasticity may be avoided and a hydrogel with high strength may be produced. It is noted that the reaction at the terminal unsaturated bond to form the crosslinked structure may be performed in the same step as the copolymerization reaction of the (meth)acrylic group, in the presence of a sufficient amount of an initiator. Even in such one step, the copolymerization reaction at a (meth)acrylic group occurs first, followed by the reaction of the terminal unsaturated bond, on account of their difference in reactivity.

In the preparation of the copolymer comprising recurring units derived from the polymerization of the compound of the present invention and from the another polymerizable (hydrophilic) monomer, the amount of the compound of the present invention may be such that mass of the recurring unit derived from the compound of the present invention is at least 10% by mass, based on the total mass of the copolymer, preferably from 10 to 80 parts by mass, more preferably from 10 to 60 parts by mass. A weight average molecular weight of the (co)polymer is not particularly limited, but preferably from 1,000 to 1,000,000, more preferably from 1,000 to 100,000, as determined by gel permeation chromatography (GPC).

Examples of the another polymerizable (hydrophilic) monomer include acrylic monomers such as (meth)acrylic acid, methyl(meth)acrylate, ethyl(meth)acrylate, (poly)ethylene glycol dimethacrylate, polyalkylene glycol mono (meth)acrylate, polyalkylene glycol monoalkyl ether (meth) acrylate, trifluoroethyl (meth)acrylate, 2-hydroxyethyl (meth)acrylate, and 2,3-dihydroxypropyl (meth)acrylate; acrylic acid derivatives such as N,N-dimethylacrylamide, N,N-diethylacrylamide, N-acryloylmorpholine, and N-methyl (meth)acrylamide; N-vinylpyrrolidone, and other unsaturated aliphatic or aromatic compounds such as crotonic acid, cinnamic acid, and vinylbenzoic acid; and siloxane monomers having a polymerizable group such as (meth)acrylic group. The monomer may be used alone or in combination thereof.

The copolymerization of the compound of the present invention with the another polymerizable monomer may be conducted in a conventional method, for example, in the presence of a known polymerization initiator such as a heat polymerization initiator or a photopolymerization initiator. Examples of the polymerization initiator include 2-hydroxy-2-methyl-1-phenyl-propan-1-one, azobisisobutyronitrile, azobisdimethylvaleronitrile, benzoyl peroxide, tert-butyl hydroperoxide, cumene hydroperoxide, and 2,2'-azobis(2-methylpropionamidine) dihydrochloride. The polymerization initiator may be used alone or in combination thereof. An amount of the polymerization initiator is preferably from 0.001 to 2 parts by mass, more preferably from 0.01 to 1 part by mass, per total 100 parts by mass of the components to be polymerized.

The polymer comprising the recurring unit derived from the compound of the present invention is excellent in hydrophilicity. The hydrogel obtained from the polymer is excellent in strength and wettability. The compound of the present invention is therefore suited for use in the preparation of medical materials such as ophthalmic devices, contact lenses, intraocular lenses, and artificial corneas. The method of preparing a medical material from the polymer is not particularly limited and may be any conventional method. For example, a cutting process or a molding process may be used for shaping the polymer into a lens, such as contact lens or intraocular lens.

EXAMPLES

The present invention will hereinafter be described more specifically with reference to the following Examples and Comparative Examples, but the present invention is not

Example 1

Step I

A 1-liter three-necked eggplant flask equipped with a Dimroth condenser and a thermometer was charged with 225.0 g of 2-(chloromethyl)-2-methyloxirane, 125.0 g of allyl alcohol, 225.0 g of n-hexane, and 68.2 g of potassium hydroxide and the resulting mixture was stirred at 20° C. for 10 hours. After completion of the reaction, the reaction mixture was washed three times with deionized water, followed by distillation at a reduced pressure to obtain a colorless, transparent liquid in a yield of 176.6 g. According to $^1$H-NMR, the product was a compound represented by the following formula (6A).

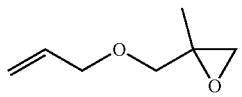

(6A)

Step II

A 300-mL three-necked eggplant flask equipped with a Dimroth condenser, a thermometer, and a dropping funnel was charged with 50.0 g of the compound of the formula (6A) obtained in Step I above, 70.0 g of methacrylic acid, and 5.0 g of sodium methacrylate. The resulting mixture was heated to 100° C. and aged for 4 hours. After the reaction, 100.0 g of toluene was added, followed by washing three times with a 2M aqueous solution of sodium hydroxide and twice with deionized water. The solvent, and unreacted raw material were distilled off at an internal temperature of 80° C. and a reduced pressure to obtain a colorless, transparent liquid in a yield of 67.3 g. According to 1H-NMR, the product was a compound represented by the following formula (6B).

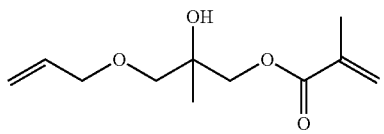

(6B)

The 1H-NMR data are as follows.

1.1 ppm(3H), 2.0 ppm(3H), 3.4 ppm(2H), 4.1 ppm(2H), 4.3 ppm(2H), 5.3 ppm(2H), 5.6 ppm(1H), 5.9 ppm(1H), 6.1 ppm(1H).

Example 2

Step I

The step I of Example 1 was repeated, except that 220.0 g of allyl glycol was used instead of allyl alcohol, to obtain a colorless transparent liquid in a yield of 180.0 g. According to $^1$H-NMR, the product was a compound represented by the following formula (7A).

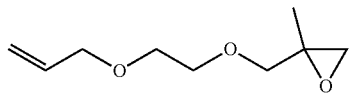

(7A)

Step II

The step II of Example 1 was repeated, except that 67.2 g of the compound represented by the formula (7A) was used instead of the compound represented by the formula (6A), to obtain a colorless, transparent liquid in a yield of 67.3 g. According to 1H-NMR, the product was a compound represented by the following formula (7B).

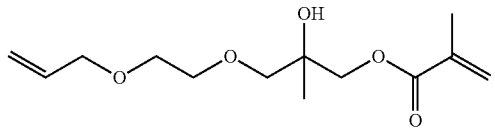

(7B)

The 1H-NMR data are as follows.

1.1 ppm(3H), 2.0 ppm(3H), 3.4 ppm(6H), 4.1 ppm(2H), 4.3 ppm(2H), 5.3 ppm(2H), 5.6 ppm(1H), 5.9 ppm(1H), 6.1 ppm(1H)

Comparative Example 1

A comparative compound used in Comparative Example 1 was a compound having a secondary hydroxyl group and represented by the following formula (a) and containing an isomer having a primary hydroxyl group and represented by the following formula (a').

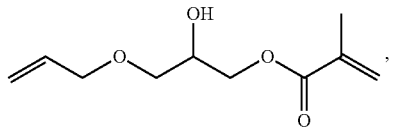

(a)

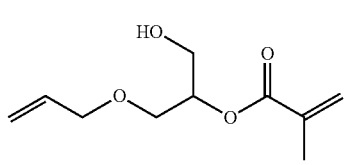

(a')

Comparative Example 2

A comparative compound used in Comparative Example 2 was allyl methacrylate (AMA) which does not have a hydroxyl group.

Preparation Examples of Hydrogel (Examples 1 and 2, and Comparative Examples 1 and 2) FIRST POLYMERIZATION Each of the compounds obtained above in the Examples and the comparative compounds, methyl methacrylate (MMA), N,N-dimethylacrylamide (DMA), N,N'-methylenebisacrylamide (MBA), and azobisisobutyronitrile (AIBN) were mixed in the ratios shown in Table 1 and stirred until the mixture became a uniform solution. After the stirring, bubbling with $N_2$ was carried out for 5 minutes for sufficient deaeration and, then, the solution was put in a mold (200 μm thick) made of polypropylene and the mold was sealed. The mold having the solution sealed therein was left to stand for curing for 4 hours in an oven of 70° C. which was in a nitrogen atmosphere. After the curing, a resin thus obtained was taken out from the mold and washed with deionized water to obtain a hydrogel film. Physical properties of the resulting film were determined according to the method described below. The results are as shown in Table 1.

Second Polymerization

The hydrogel film obtained in the first polymerization step was immersed in a 1% aqueous solution of 2,2'-azobis(2-methylpropionamidine) dihydrochloride (V-50) for 4 hours and left to sand for 6 hours in an oven of 70° C. which was in a nitrogen atmosphere to proceed further with polymerization (curing). The hydrogel film thus obtained was washed with 2-propanol and deionized water. The physical properties of the film were determined in the method described below. The results are as shown in Table 1.

Preparation Examples of Hydrogel (Examples 3 and 4 and Comparative Examples 3 and 4)

Each of the compounds obtained in the Examples and the comparative compounds, methyl methacrylate (MMA), N,N-dimethylacrylamide (DMA), N,N'-methylenebisacrylamide (MBA), and azobisisobutyronitrile (AIBN) were mixed in the ratios shown in Table 2 and stirred until the mixture became a uniform solution. After the stirring, bubbling with $N_2$ was carried out for 5 minutes for sufficient deaeration and, then, the solution was put in a mold (200 μm thick) made of polypropylene and the mold was sealed. The mold having the solution sealed therein was left to stand for 8 hours in an oven of 70° C. which was in a nitrogen atmosphere to cure the solution. After the curing, a resulting resin was taken out from the mold and washed with 2-propanol and deionized water to obtain a hydrogel film. Physical properties of the film thus obtained were determined in the method described below. The results are as shown in Table 2.

Equilibrium Water Content

The film was immersed in deionized water at 25° C. for 48 hours, water was wiped off from the film surface, and the mass of the hydrated film was measured. Then, the hydrated film was dried in an oven of 50° C. for 48 hours and in an oven of 25° C. for 24 hours and the mass of the dried film was measured. The equilibrium water content was calculated according to the following formula:

Equilibrium water content (%)=100×[{(mass of the hydrated film)−(mass of the dried film)}/(mass of the hydrated film)]

Elastic Modulus

The film was immersed in deionized water at 25° C. for 48 hours, water was wiped off from the film surface to prepare a hydrated film. A Young's modulus of elasticity of the hydrated film was determined using Instron 5943, as follows. A sample piece of 0.8 cm×4.0 cm obtained by cutting the hydrated film was elongated with a load cell of 50 N at a head speed of 1 cm/min and an initial-stage (linear portion) slope of a stress-strain curve was determined in a graph with the stress in the ordinate and the strain in the abscissa. The slope is a Young's modulus of elasticity (MPa).

TABLE 1

| | | Example 1 | Example 2 | Comparative Example 1 | Comparative Example 2 |
|---|---|---|---|---|---|
| Compound | 6B | 10 | — | — | — |
| | 7B | — | 10 | — | — |
| Comparative Compound | AHPM | — | — | 10 | — |
| | AMA | — | — | — | 10 |
| Polymerizable monomer | MMA | 40 | 40 | 40 | 40 |
| | DMA | 48 | 48 | 48 | 48 |
| | MBA | 2 | 2 | 2 | 2 |
| | AIBN | 0.05 | 0.05 | 0.05 | 0.05 |
| | V-50 | 1 | 1 | 1 | 1 |
| | Water | 30 | 30 | 30 | 30 |
| Evaluation, After the first polymerization | Equilibrium water content, % | 55 | 58 | 55 | 41 |
| | Elastic Modulus, MPa | 2.3 | 2 | 2.1 | 2.1 |
| Evaluation, After the second polymerization | Equilibrium water content, % | 52 | 54 | 43 | 40 |
| | Elastic Modulus, MPa | 2.8 | 2.8 | 4.5 | 2.7 |

TABLE 2

| | | Example 3 | Example 4 | Comparative Example 3 | Comparative Example 4 |
|---|---|---|---|---|---|
| Compound | 6B | 10 | — | — | — |
| | 7B | — | 10 | — | — |
| Comparative Compound | AHPM | — | — | 10 | — |
| | AMA | — | — | — | 10 |
| Polymerizable monomer | MMA | 40 | 40 | 40 | 40 |
| | DMA | 48 | 48 | 48 | 48 |
| | MBA | 2 | 2 | 2 | 2 |
| | AIBN | 1 | 1 | 1 | 1 |
| Evaluation | Equilibrium water content, % | 53 | 53 | 41 | 37 |
| | Elastic Modulus, MPa | 2.7 | 2.6 | 4.4 | 2.7 |

As seen in Table 1, the hydrogel obtained using the comparative compound having the secondary and primary hydroxyl groups showed the drastic reduction in equilibrium water content and, further, the marked increase in modulus of elasticity after the second polymerization. The hydrogel obtained using the comparative compound having no hydroxyl group had the low equilibrium water content and the insufficient hydrophilicity. On the other hand, the hydrogel obtained using the compound of the present invention having a tertiary hydroxyl group had the high equilibrium water content and, even after the second polymerization, the decrease in equilibrium water content was small.

These are because the secondary and primary hydroxyl groups in the compound of Comparative Example 1 causes a reaction in the stage of the polymerization of an unsaturated bond; meanwhile, the tertiary hydroxyl group does not cause a reaction. Since the compound of the present invention does not cause an unintended crosslinking reaction at the hydroxyl group, a hydrogel obtained from the compound shows less reduction in an equilibrium water content and prevention of undesired increase in a modulus of elasticity.

As seen in Table 2, similar results are achieved also in the case where the polymerization at a (meth)acrylic group and the reaction of an unsaturated bond are carried out in one step.

Thus, the hydrogel obtained using the compound of the present invention has both of the useful hydrophilicity and the sufficient strength.

INDUSTRIAL APPLICABILITY

The hydrogel obtained using the compound of the present invention has improved hydrophilicity and strength. The compound of the present invention is useful as a monomer to prepare medical materials such as ophthalmic devices, contact lenses, intraocular lenses, artificial corneas and eyeglass lenses.

The invention claimed is:

1. A compound represented by the following formula (1):

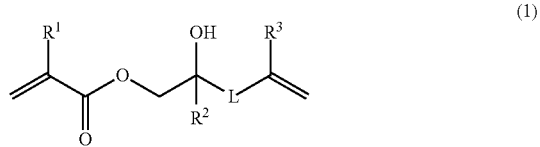

wherein $R^1$ is a hydrogen atom or a methyl group, $R^2$ is a monovalent hydrocarbon group having 1 to 6 carbon atoms, $R^3$ is a hydrogen atom or a methyl group and, L is a divalent hydrocarbon group having 2 to 10 carbon atoms and optionally having an ether bond.

2. The compound according to claim 1, wherein $R^1$ is a methyl group.

3. The compound according to claim 1, wherein L is represented by the following formula (2):

wherein the sites marked with * or ** is bonded to the carbon atom and n is 1 or 2.

4. The compound according to claim 1, wherein $R^2$ is a methyl group.

5. The compound according to claim 2, wherein L is represented by the following formula (2):

wherein the sites marked with * or ** is bonded to the carbon atom and n is 1 or 2.

6. The compound according to claim 2, wherein $R^2$ is a methyl group.

7. The compound according to claim 3, wherein $R^2$ is a methyl group.

8. A (co)polymer comprising repeating units derived from polymerization at the (meth)acryl group of the compound according to claim 1.

9. The (co)polymer according to claim 8, wherein an amount of said repeating units is 10 mass % or more, based on a mass of the (co)polymer.

10. A (co)polymer comprising repeating units derived from polymerization at the (meth)acryl group of the compound according to claim 2.

11. The (co)polymer according to claim 10, wherein an amount of said repeating units is 10 mass % or more, based on a mass of the (co)polymer.

12. A (co)polymer comprising repeating units derived from polymerization at the (meth)acryl group of the compound according to claim 3.

13. The (co)polymer according to claim 12, wherein an amount of said repeating units is 10 mass % or more, based on a mass of the (co)polymer.

14. A (co)polymer comprising repeating units derived from polymerization at the (meth)acryl group of the compound according to claim 4.

15. A hydrogel comprising the (co)polymer according to claim 8.

16. A medical material comprising the (co)polymer according to claim 8.

17. A method for preparing a compound represented by the following formula (1):

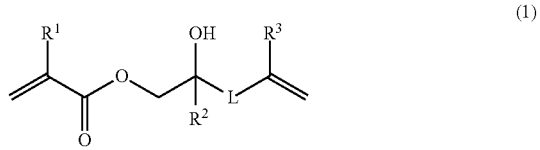

wherein $R^1$ is a hydrogen atom or a methyl group, $R^2$ is a monovalent hydrocarbon group having 1 to 6 carbon atoms, $R^3$ is a hydrogen atom or a methyl group and, L is a divalent hydrocarbon group having 2 to 10 carbon atoms and optionally having an ether bond, comprising a step of reacting an epoxy compound represented by the following formula (3):

wherein $R^2$, $R^3$ and L are as defined above, with a (meth)acrylic acid to obtain the compound represented by the formula (1).

18. The method according to claim 17, wherein $R^1$ is a methyl group, L is represented by the following formula (2):

wherein the sites marked with * or ** is bonded to the carbon atom and n is 1 or 2.

* * * * *

UNITED STATES PATENT AND TRADEMARK OFFICE
CERTIFICATE OF CORRECTION

PATENT NO. : 11,919,987 B2
APPLICATION NO. : 17/270940
DATED : March 5, 2024
INVENTOR(S) : Kaoru Okamura It is certified that error appears in the above-identified patent and that said Letters Patent is hereby corrected as shown below:

In the Specification

Column 4, Line 63: Please correct "(2')" to read --(2")--

Column 9, Line 2: Please correct "1H-NMR" to read --$^1$H-NMR--

Column 9, Line 41: Please correct "1H-NMR" to read --$^1$H-NMR--

Column 9, Line 54: Please correct "1H-NMR" to read --$^1$H-NMR--

Column 10, Line 13: Please correct "1H-NMR" to read --$^1$H-NMR--

Column 10, Line 25: Please correct "1H-NMR" to read --$^1$H-NMR--

Column 10, Lines 59-60: Please add a paragraph break before and after "FIRST POLYMERIZATION"

Signed and Sealed this
Twenty-third Day of July, 2024

Katherine Kelly Vidal
*Director of the United States Patent and Trademark Office*